(12) United States Patent
Kishi et al.

(10) Patent No.: US 6,986,998 B2
(45) Date of Patent: Jan. 17, 2006

(54) METHOD OF ANALYZING COMPONENTS IN BIOLOGICAL SAMPLES

(75) Inventors: Koji Kishi, Kobe (JP); Tsutomu Kakuyama, Kobe (JP); Koji Ochiai, Kobe (JP)

(73) Assignee: International Reagents Corporation, Hyogo (JP)

( * ) Notice: Subject to any disclaimer, the term of this patent is extended or adjusted under 35 U.S.C. 154(b) by 443 days.

(21) Appl. No.: 10/297,241

(22) PCT Filed: Jun. 5, 2001

(86) PCT No.: PCT/JP01/04721

§ 371 (c)(1),
(2), (4) Date: Dec. 3, 2002

(87) PCT Pub. No.: WO01/94619

PCT Pub. Date: Dec. 13, 2001

(65) Prior Publication Data

US 2003/0129681 A1  Jul. 10, 2003

(51) Int. Cl.
*C12Q 1/60* (2006.01)
*C12Q 1/44* (2006.01)
*C12Q 1/26* (2006.01)
*C12Q 1/28* (2006.01)
*G01N 33/53* (2006.01)

(52) U.S. Cl. .................... 435/11; 435/19; 435/25; 435/26; 435/28; 435/975

(58) Field of Classification Search ............... 435/11, 435/19, 25, 26, 28, 975
See application file for complete search history.

(56) References Cited

U.S. PATENT DOCUMENTS

| 6,114,134 A * | 9/2000 | Kishi et al. ............... 435/11 |
| 2003/0129681 A1 * | 7/2003 | Kishi et al. ............... 435/11 |

FOREIGN PATENT DOCUMENTS

| EP | 1 020 532 A1 | 7/2000 |
| JP | 9-43234 | 2/1997 |
| JP | 11-9300 | 1/1999 |
| WO | WO 98/59068 | 12/1998 |

OTHER PUBLICATIONS

Hart et al, Infection & Immunity, V. 64(4), pp 1491-1493, (Apr., 1996).*

* cited by examiner

*Primary Examiner*—Louise N. Leary
(74) *Attorney, Agent, or Firm*—Kilyk & Bowersox, P.L.L.C.

(57) ABSTRACT

There is provided a method for a selective assay of component, particularly cholesterol, in very low-density lipoprotein (VLDL) which is one of serum lipoproteins.

In the assay, an enzymatic reaction of lipoprotein lipase (LPL) or cholesterol esterase (CE) which well reacts with high-density lipoprotein (HDL) and VLDL is carried out at least in the presence of calixarene or a salt thereof. It is also carried out in the presence of one or more substance(s) selected from albumin and basic amino acids in addition to calixarene or a salt thereof.

20 Claims, No Drawings

METHOD OF ANALYZING COMPONENTS IN BIOLOGICAL SAMPLES

This application claims the benefit of earlier filed International Application No. PCT/JP01/04721 filed Jun. 5, 2001.

TECHNICAL FIELD

The present invention relates to a method for the assay of components in very low-density lipoprotein (VLDL) in blood. More particularly, it relates to a method for the selective assay of cholesterol in VLDL.

BACKGROUND ART

Regarding lipoprotein, serum contains four kinds of lipoprotein, i.e. high-density lipoprotein (HDL), low-density lipoprotein (LDL), very low-density lipoprotein (VLDL) and chylomicron (CM). It has been known that diseases such as various types of hyperlipemia are derived from an increase in one or more of such lipoprotein fractions and there have been reported methods for a quantitative determination by fractionation into each lipoprotein.

Fractionation of lipoprotein has been carried out by means of an ultracentrifugal operation from ancient days. The operation therefor needs skillfulness and is conducted by installing an ultracentrifuge separately and centrifugation is carried out for several days. Therefore, it was not possible to treat many samples. Besides that, there are a method where lipoprotein is separated by electrophoresis and amount of protein is determined and a method for the assay of cholesterol for each lipoprotein by HPLC but they are lacking in processing ability and, in addition, expensive apparatus in addition to the popular automatic analysis apparatus is necessary.

Recently, in order to solve the above-mentioned problem concerning the assay of cholesterol in HDL, a fully automatic kit for the assay of cholesterol in HDL has been developed and is diffusing. The art mentioned in Japanese Patent No. 2,600,065 (Nov. 30, 1994), Japanese Patent Laid-Open No. 08/201,393 (Jan. 31, 1995) and Japanese Patent Laid-Open No. 08/131,195 (Dec. 21, 1994) use a fractionating agent together but metal used as divalent cation contained in the fractionating agent forms an insoluble precipitate with detergent which is commonly used in an full-automatic analyzing apparatus and that is accumulated in a waste liquid mechanism causing a trouble. In addition, an insoluble aggregate is formed during the reaction resulting in turbidity which affects the assayed result and causes the assay error and, further, reaction cell is polluted by the aggregate which significantly affects the assayed result for other biochemical items being assayed at the same time.

There are many cases that the reaction is completed within 10 minutes in most of the popular automatic analyzing apparatuses. Moreover, it is possible to select two-point end method, rate method, double rate method, fix time method, etc. which are known methods and, therefore, assay is possible even in a turbid state. However, such an assay in a turbid state causes an error in the assayed data if there are changes in turbidity during the reaction and there is a problem in precision. In addition, reproducibility lowers when the reaction solution becomes turbid. Therefore, there is a limitation in the sample to be assayed and it is not possible to cope with broad assaying wavelengths and various kinds of samples of patients. For example, near 340 nm (UV region), there is a disadvantage that absorbance becomes 2~3 or more due to a turbid phenomenon by the aggregate and is sometimes out of the allowable range of the analyzer. An art of Japanese Patent Laid-Open No. 09/96,637 (Jul. 19, 1996) where no divalent cation is used is a method where anti-serum aggregating with lipoprotein is contained but even the method forms a hardly soluble antigen-antibody aggregate and, therefore, the reaction cell is polluted. Accordingly, that greatly affects the assayed data for other biochemical items assayed at the same time. Further, since turbidity in the reaction solution becomes strong, precise assay is impossible by the same reason as above for the assay of cholesterol in HDL especially by UV region.

Such an art comprises a device for assaying method and common technique for inhibiting the enzymatic reaction by the formation of complex and aggregate and the bad affection inherent to the turbidity is not solved.

With regard to assay of cholesterol in LDL (LDL-C), there are reports for an assaying method of LDL-C with an object of full automation as noted in the art of Japanese Patent Laid-Open No. 07/280,812 (Apr. 5, 1994), WO 96/29599 (Mar. 20, 1995) and Japanese Patent Laid-Open No. 09/313,200 (May 29, 1996). Like the assay of cholesterol in HDL (HDL-C), those assaying methods are on the extension line of the above-mentioned art forming aggregate and complex and, therefore, it is a matter to be solved in future how the turbidity is treated.

On the other hand, in the test and diagnosis of the lipoprotein-related diseases such as hyperlipemia, information concerning HDL-C and LDL-C only is insufficient as clinical information. The World Health Organization (WHO) classifies hyperlipemia into five types [*Rinsho Kensa*, Vol.40, No. 9, page 107 (1996)] in which fate of cholesterol in VLDL (VLDL-C) is stipulated as well. Thus, for example, in the type IIa among the hyperlipemia II, LDL rises while, in the type IIb, LDL and VLDL rise. In the type IV, VLDL decreases while, in the type V, VLDL rises. As such, hyperlipemia is unable to be judged by the fate of single lipoprotein. Further, in the study concerning lipoprotein metabolism of coronary artery diseases such as arteriosclerosis caused by hyperlipemia, information for VLDL-C has also become necessary. Furthermore, there is a report that the fate of remnant-like lipoprotein (RLP) is a direct trigger for arteriosclerosis [McNamara J. R., et al., *Clin. Chem.*, 44, 1224–1232 (1998)]. Assay of not only VLDL-C but also VLDL sub-fraction such as RLP-C is being regarded as important. Anyway, there is no assaying method where an operation for the separation of VLDL-C is unnecessary and, at present, there is no way but relying upon ultracentrifugation, electrophoresis, HPLC, etc. Accordingly, that is a cause of no progress in the study in spite of its clinical significance.

DISCLOSURE OF THE INVENTION

An object of the present invention is to provide a method for a selective assay of components, particularly cholesterol, in VLDL which is one of serum lipoproteins.

In view of such circumstances, the present inventors have carried out intensive investigations for a quantitative determination of the components in VLDL in biological samples, particularly in serum, using a commonly used automatic analysis apparatus without separation by means of centrifugal separation and without forming turbidity by complex or aggregate in the reaction solution. As a result, they have found a method for assaying the VLDL-C without formation of complex or aggregate which is turbidity causing the assay error that an enzymatic reaction by lipoprotein lipase (LPL) or cholesterol esterase (CE) dominantly and directly acting on the VLDL is carried out in the presence of at least calixarene or a salt thereof, particularly in the presence of at least calixarene or a salt thereof and albumin and/or basic amino acid and, as a result, the present invention. has been achieved.

Thus, the present invention comprises (1) a method for assaying the components in very low-density lipoprotein (VLDL) fraction by an enzymatic reaction, the method which is characterized in that a reaction by enzyme showing a high specificity to VLDL is carried out under the control by addition of at least calixarene or a salt thereof; (2) the method for assaying the component in VLDL according to the above (1) wherein the reaction by enzyme is carried out under the control by addition of at least albumin in addition to the calixarene or the salt thereof; (3) the method for assaying the component in VLDL according to the above (1) wherein the reaction by enzyme is carried out under the control by addition of at least basic amino acid in addition to the calixarene or the salt thereof; (4) the method for assaying the component in VLDL according to the above (1) wherein the reaction by enzyme is carried out under the control by addition of at least albumin and basic amino acid in addition to the calixarene or the salt thereof; (5) the method for assaying the component in VLDL according to any of the above (1) to (4) wherein the enzyme showing a high specificity to VLDL is lipoprotein lipase (LPL) and/or cholesterol esterase (CE) derived from *Chromobacterium* or *Pseudomonas*; (6) the method for assaying the component in VLDL according to any of the above (1) to (5) wherein the component in VLDL to be assayed is cholesterol, the enzymatic reaction for the assay of cholesterol use cholesterol dehydrogenase and oxidizing coenzyme, and a reduced coenzyme which is a product of the enzymatic reaction is spectrometrically detected; (7) the method for assaying the component in VLDL according to any of the above (1) to (5) wherein the component in VLDL to be assayed is cholesterol, the enzymatic reaction for the assay of cholesterol use cholesterol oxidase, and hydrogen peroxide which is a product of the enzymatic reaction is spectrometrically detected using peroxidase; (8) a reagent kit equipped with reagents necessary for conducting the method for assaying the component in VLDL according to any of the above (1) to (7); and (9) a method for the manufacture of the reagent kit mentioned in the above (8).

BEST MODE FOR CARRYING OUT THE INVENTION

The present invention will now be illustrated in detail as hereunder.

With regard to an enzyme which acts on lipoprotein to hydrolyze whereby the components of lipoprotein are liberated, there is cholesterol ester hydrolase such as LPL or CE. Among them, LPL or CE which is derived for example from *Chromobacterium viscosum* or *Pseudomonas* is preferably used since it dominantly reacts with VLDL as compared with other lipoproteins. Even an enzyme which is modified, for example, with an object of stabilization of the enzyme may be used so far as it is an enzyme dominantly reacting with VLDL and able to achieve the object of the present invention. Therefore, there is no particular limitation whether or not it is modified.

When calixarenes are added, reactivity of LPL and CE with LDL can be suppressed and substrate specificity of such an enzyme is improved. Calixarene suppresses the reactivity of LPL and CE with LDL when it is bonded to near sugar chain and fatty acid of the surface of LDL. With regard to calixarene, there are listed calixarene and a salt thereof such as calix[4]arene, calix[6]arene, calix[8]arene, calix[4]arene sulfate, calix[6]arene sulfate, calix[8]arene sulfate, calix[4] arene acetate, calix[6]arene acetate, calix[8]arene acetate, carboxycalix[4]arene, carboxycalix[6]arene, carboxycalix [8]arene, calix[4]areneamine, calix[6]areneamine and calix [8]areneamine. Appropriate one may be selected therefrom and the concentration for actual use may be decided by simple experimental repetition. One or more kind(s) of calixarene may be used for the method of assay according to the present invention.

In the method of assay according to the present invention, it is preferred to use albumin in addition to calixarenes. LPL or CE having selectivity to VLDL inherently acts on HDL as well. Thus, LPL or CE shows a high reactivity with HDL and VLDL while it weakly reacts with LDL. When albumin is added, the reactivity of LPL or CE with HDL is suppressed whereupon the enzyme reacts only with VLDL. Bovine serum albumin is usually used as albumin although there is no particular limitation for its origin. Concentration in actual may be determined by experiments and the range of 0.05~10% is usable.

Similarly, it is possible to suppress the reaction with HDL using a basic amino acid. Thus, in the method of assay according to the present invention, it is possible to use a basic amino acid and calixarene together or to use calixarene and albumin together. It is more preferred in the present invention that albumin and a basic amino acid are used together in addition to calixarene.

With regard to a basic amino acid, there may be usually used arginine, arginine hydrochloride, lysine, lysine hydrochloride, histidine, histidine hydrochloride, hydroxylysine and hydroxylysine hydrochloride and they may be appropriately selected and used. Concentration in actual may be determined by experiments and the range of 0.1~1,000 mmol/L is usable. One or more kind(s) of basic amino acid may be used for the method of assay according to the present invention.

When the component to be assayed in VLDL is cholesterol, assay of cholesterol is carried out in accordance with the common method for assaying the total cholesterol. For example, there has been known a method where cholesterol is made to react with cholesterol dehydrogenase (CDH) and oxidized coenzyme and the reduced coenzyme which is a product of the said reaction is spectrometrically detected. CDH requires hydrazine for potentiating the quantifying property of the reaction [an art of Japanese Patent Laid-Open No. 05/176,797 (Dec. 27, 1991)] and is used by combining with other conditions such as activator and stabilizer. Known art may be applied therefor. For example, activators and stabilizers are nonionic surface-active agents and cholic acids. Concentration thereof in actual may be determined by experiments. Examples of the oxidized coenzyme are oxidized β-nicotinamide adenine dinucleotide (NAD), oxidized thio-nicotinamide adenine dinucleotide (t-NAD), oxidized β-nicotinamide adenine dinucleotide phosphate (NADP) and oxidized thio-nicotinamide adenine dinucleotide phosphate (t-NADP).

It is also possible to use a method where cholesterol is made to react with cholesterol oxidase (COD) and hydrogen peroxide which is a product of the said reaction is spectrometrically detected using peroxidase. With regard to a method for quantitative determination of hydrogen peroxide using peroxidase, known methods may be used. When the assay is carried out using COD, activators and stabilizers for enzyme are appropriately selected and used as same as in the case of the assay using CDH. Conditions such as concentration in actual use may be determined by experiments.

The present invention further provides a reagent kit equipped with reagents necessary for carrying out the above-mentioned method for assaying the components in VLDL according to the present invention. The reagent kit of the present invention contains one or more substances selected at least from calixarenes, albumin and basic amino acids and is a reagent kit for the assay of the components in the manufactured VLDL.

EXAMPLES

As hereinafter, a method for the assay of cholesterol in VLDL will be illustrated in more detail by way of Examples although the present invention is not limited thereto.

Example 1

The following reagents were prepared. With regard to the samples, 30 human serum examples from volunteers were used. The assay was carried out using an Automatic Analysis Apparatus, Type 7170, of Hitachi. Firstly, 180 μL of the reagent 1 were added to 18 μL of the sample followed by keeping at 37° C. for 5 minutes and, at that stage, absorbance 1 was measured at the dominant wavelength of 340 nm and non-dominant wavelength of 570 nm. Then 60 μL of the reagent 2 were added followed by keeping at 37° C. for 5 minutes and, at that stage, absorbance 2 was measured at the dominant wavelength of 340 nm and non-dominant wavelength of 570 nm. Difference between the absorbance 1 and the absorbance 2 was calculated and converted to the amount of the sample using a control of known VLDL-cholesterol concentration as a standard solution.

The control method was in accordance with a method by Havel et al. [Have R J, Eder H A, Bragdon J H: The distribution and chemical composition of ultracentrifugally separated lipoproteins in human serum, *J. Clin. Invest.*, 34, 1345~1353 (1955)]. Cholesterol in the fractionated VLDL fraction was determined by a T-CHO reagent L "Kokusai" (International Reagents Corporation). Table 1 shows the result of assay using 30 cases of human serum. In the present method, the correlation coefficient was 0.993 (p<0.05) and the result was good well coinciding with the control method.

| Reagent 1 | |
|---|---|
| HEPES buffer (pH 7.5) | 50 mmol/L |
| Hydrazinium dichloride | 60 mmol/L |
| Sodium cholate (activator) | 0.4% |
| Oxidized β-nicotinamide adenine dinucleotide | 6.0 mmol/L |
| Calix[8]arene sulfate | 10.0 mmol/L |
| Bovine serum albumin | 2.0% |
| Arginine | 200 mmol/L |
| Reagent 2 | |
| HEPES buffer (pH 8.0) | 50 mmol/L |
| Cholesterol dehydrogenase | 20 U/mL |
| Cholesterol ester hydrolase (derived from Pseudomonas sp.) | 3 U/mL |
| Sodium cholate | 0.1% |

Example 2

The following reagents were prepared. With regard to the samples, 10 human serum examples from normal healthy persons were used. The assay was carried out using an Automatic Analysis Apparatus, Type 7170, of Hitachi. Firstly, 180 μL of the reagent 3 were added to 15 μL of the sample followed by keeping at 37° C. for 5 minutes and, at that stage, absorbance 1 was measured at the dominant wavelength of 600 nm and non-dominant wavelength of 700 nm. Then 60 μL of the reagent 4 were added followed by keeping at 37° C. for 5 minutes and, at that stage, absorbance 2 was measured at the dominant wavelength of 360 nm and non-dominant wavelength of 700 nm. Difference between the absorbance 1 and the absorbance 2 was calculated and converted to the amount of the sample using a control of known VLDL-cholesterol concentration as a standard solution. The control method used was as same as that in Example 1. Table 2 shows the result of assay using 30 cases of human serum. In the present method, the correlation coefficient was 0.997 (p<0.05) and the result was good well coinciding with the control method.

| Reagent 3 | |
|---|---|
| MES buffer (pH 6.5) | 50 mmol/L |
| HDAOS | 2.0 mmol/L |
| Emulgen 913 (activator) | 0.02% |
| Sodium cholate (activator) | 0.5% |
| Calix[8]arene sulfate | 10.0 mmol/L |
| Bovine serum albumin | 1.5% |
| Ascorbic acid oxidase | 3 U/mL |
| Arginine | 200 mmol/L |
| Reagent 4 | |
| MES reagent (pH 6.5) | 50 mmol/L |
| Cholesterol oxidase | 2 U/mL |
| Cholesterol ester hydrolase derived from *Chromobacterium viscosum* | 3 U/mL |
| 4-Aminoantipyrine | 10 mmol/L |
| Sodium cholate | 0.1% |
| Peroxidase | 15 U/mL |

TABLE 1

(unit: mg/dL)

| Samples | Control Method | Present Method |
|---|---|---|
| 1 | 1.2 | 9.1 |
| 2 | 2.2 | 8.4 |
| 3 | 4.6 | 5.7 |
| 4 | 25.2 | 25.2 |
| 5 | 231.2 | 242.0 |
| 6 | 5.8 | 7.5 |
| 7 | 1.4 | 14.4 |
| 8 | 25.4 | 38.5 |
| 9 | 9.6 | 19.3 |
| 10 | 4.0 | 16.2 |
| 11 | 6.2 | 13.2 |
| 12 | 2.0 | 4.6 |
| 13 | 13.4 | 15.4 |
| 14 | 5.8 | 14.2 |
| 15 | 23.6 | 20.1 |
| 16 | 2.6 | 2.9 |
| 17 | 1.2 | 2.2 |
| 18 | 21.6 | 20.1 |
| 19 | 1.2 | 11.0 |
| 20 | 16.9 | 28.0 |
| 21 | 32.4 | 42.0 |
| 22 | 50.8 | 57.0 |
| 23 | 87.4 | 90.5 |
| 24 | 104.9 | 99.4 |
| 25 | 129.0 | 114.4 |
| 26 | 142.0 | 134.9 |
| 27 | 165.3 | 154.8 |

TABLE 1-continued (unit: mg/dL)

| Samples | Control Method | Present Method |
|---|---|---|
| 28 | 45.1 | 56.2 |
| 29 | 31.3 | 40.1 |
| 30 | 23.1 | 35.7 |
| Correlation Coefficient | | 0.993 |
| Inclination of Regression Line | | 0.947 |
| Intercept of Regression Line | | 6.364 |

TABLE 2

(unit: mg/dL)

| Samples | Control Method | Present Method |
|---|---|---|
| 1 | 1.2 | 4.6 |
| 2 | 2.2 | 4.5 |
| 3 | 4.6 | 6.4 |
| 4 | 25.2 | 25.2 |
| 5 | 231.2 | 250.6 |
| 6 | 5.8 | 8.0 |
| 7 | 1.4 | 4.4 |
| 8 | 25.4 | 27.9 |
| 9 | 9.6 | 9.6 |
| 10 | 4.0 | 6.6 |
| 11 | 6.2 | 3.9 |
| 12 | 2.0 | 5.4 |
| 13 | 13.4 | 16.2 |
| 14 | 5.8 | 4.5 |
| 15 | 23.6 | 20.2 |
| 16 | 2.6 | 4.6 |
| 17 | 1.2 | 3.2 |
| 18 | 21.6 | 20.5 |
| 19 | 1.2 | 1.7 |
| 20 | 16.9 | 17.7 |
| 21 | 32.4 | 33.9 |
| 22 | 50.8 | 57.4 |
| 23 | 87.4 | 81.4 |
| 24 | 104.9 | 101.2 |
| 25 | 129.0 | 119.3 |
| 26 | 142.0 | 144.4 |
| 27 | 165.3 | 160.0 |
| 28 | 45.1 | 44.6 |
| 29 | 31.3 | 29.7 |
| 30 | 23.1 | 24.9 |
| Correlation Coefficient | | 0.997 |
| Inclination of Regression Line | | 1.012 |
| Intercept of Regression Line | | 0.398 |

INDUSTRIAL APPLICABILITY

The invention established as such provides a method for the assay of the component, particularly cholesterol, in VLDL which is one of serum lipoproteins and, since measurement of amount of the component, particularly cholesterol, in VLDL can be carried out selectively and easily, it is useful for clinical test, investigation, etc. for diseases which are related to lipoprotein such as hyperlipemia.

What is claimed is:

1. A method for assaying components in a very low-density lipoprotein (VLDL) fraction of a biological sample by an enzymatic reaction, comprising the steps of
carrying out an enzyme reaction in the biological sample with an enzyme that selectively acts on VLDL in preference to other lipoproteins in the biological sample to release at least one component of the VLDL fraction, and wherein the enzyme reaction is carried out with the addition of at least calixarene or a salt thereof, and
detecting the released component.

2. The method for assaying according to claim 1, wherein the enzyme reaction is carried out by addition of at least albumin in addition to the calixarene or the thereof.

3. The method for assaying according to claim 1, wherein the enzyme reaction is carried out by addition of at least basic amino acid in addition to the calixarene or the salt thereof.

4. The method for assaying according to claim 1, wherein the enzyme reaction is carried out by addition of at least albumin and basic amino acid in addition to the calixarene or the salt thereof.

5. The method for assaying according to claim 1, wherein the enzyme that selectively acts on VLDL is lipoprotein lipase (LPL) and/or cholesterol esterase (CE) derived from *Chromobacterium* or *Pseudomonas*.

6. The method for assaying according to claim 1, wherein the component in said VLDL to be assayed is cholesterol, and wherein cholesterol released by the enzymatic reaction with VLDL is detected by an enzymatic reaction of cholesterol with cholesterol dehydrogenase and an oxidizing coenzyme followed by the spectrometric detection of a reduced coenzyme that is a product of the enzymatic reaction of cholesterol with cholesterol dehydrogenase and the oxidizing coenzyme.

7. The method for assaying according to claim 1, wherein the component in VLDL to be assayed is cholesterol, and wherein cholesterol released by the enzymatic reaction with VLDL is detected by an enzymatic reaction of cholesterol with cholesterol oxidase followed by the spectrometric detection using peroxidase of hydrogen peroxidase that is a product of the enzymatic reaction of cholesterol with cholesterol oxidase.

8. A reagent kit for releasing a component of VLDL in the assay method of claim 1 wherein the reagent kit comprises an enzyme that selectively acts on VLDL in preference to other lipoproteins and at least one of calixarene or salt thereof, albumin, or basic amino acid, or combinations thereof.

9. A method for the manufacture of the reagent kit mentioned in claim 8, the method comprising combining an enzyme that selectively acts on VLDL in preference to other lipoproteins and at least one of calixarene or salt thereof, albumin, or basic amino acid, or combinations thereof.

10. The method for assaying according to claim 2, wherein the enzyme that selectively acts on VLDL is lipoprotein lipase (LPL) and/or cholesterol esterase (CE) derived from *Chromobacterium* or *Pseudomonas*.

11. The method for assaying according to claim 3, wherein the enzyme that selectively acts on VLDL is lipoprotein lipase (LPL) and/or cholesterol esterase (CE) derived from *Chromobacterium* or *Pseudomonas*.

12. The method for assaying according to claim 4, wherein the enzyme that selectively acts on VLDL is lipoprotein lipase (LPL) and/or cholesterol esterase (CE) derived from *Chromobacterium* or *Pseudomonas*.

13. The method for assaying according to claim 2, wherein the component in said VLDL to be assayed is cholesterol, and wherein cholesterol released by the enzymatic reaction with VLDL is detected by an enzymatic reaction of cholesterol with cholesterol dehydrogenase and an oxidizing coenzyme followed by the spectrometric detection of a reduced coenzyme that is a product of the enzymatic reaction of cholesterol with cholesterol dehydrogenase and the oxidizing coenzyme.

14. The method for assaying according to claim 3, wherein the component in said VLDL to be assayed is cholesterol, and wherein cholesterol released by the enzymatic reaction with VLDL is detected by an enzymatic reaction of cholesterol with cholesterol dehydrogenase and an oxidizing coenzyme followed by the spectrometric detection of a reduced coenzyme that is a product of the enzymatic reaction of cholesterol with cholesterol dehydrogenase and the oxidizing coenzyme.

15. The method for assaying according to claim 4, wherein the component in said VLDL to be assayed is cholesterol, and wherein cholesterol released by the enzymatic reaction with VLDL is detected by an enzymatic reaction of cholesterol with cholesterol dehydrogenase and an oxidizing coenzyme followed by the spectrometric detection of a reduced coenzyme that is a product of the enzymatic reaction of cholesterol with cholesterol dehydrogenase and the oxidizing coenzyme.

16. The method for assaying according to claim 5, wherein the component in said VLDL to be assayed is cholesterol, and wherein cholesterol released by the enzymatic reaction with VLDL is detected by an enzymatic reaction of cholesterol with cholesterol dehydrogenase and an oxidizing coenzyme followed by the spectrometric detection of a reduced coenzyme that is a product of the enzymatic reaction of cholesterol with cholesterol dehydrogenase and the oxidizing coenzyme.

17. The method for assaying according to claim 2, wherein the component in VLDL to be assayed is cholesterol, and wherein cholesterol released by the enzymatic reaction with VLDL is detected by an enzymatic reaction of cholesterol with cholesterol oxidase followed by the spectrometric detection using peroxidase of hydrogen peroxidase that is a product of the enzymatic reaction of cholesterol with cholesterol oxidase.

18. The method for assaying according to claim 3, wherein the component in VLDL to be assayed is cholesterol, and wherein cholesterol released by the enzymatic reaction with VLDL is detected by an enzymatic reaction of cholesterol with cholesterol oxidase followed by the spectrometric detection using peroxidase of hydrogen peroxidase that is a product of the enzymatic reaction of cholesterol with cholesterol oxidase.

19. The method for assaying according to claim 4, wherein the component in VLDL to be assayed is cholesterol, and wherein cholesterol released by the enzymatic reaction with VLDL is detected by an enzymatic reaction of cholesterol with cholesterol oxidase followed by the spectrometric detection using peroxidase of hydrogen peroxidase that is a product of the enzymatic reaction of cholesterol with cholesterol oxidase.

20. The method for assaying according to claim 5, wherein the component in VLDL to be assayed is cholesterol, and wherein cholesterol released by the enzymatic reaction with VLDL is detected by an enzymatic reaction of cholesterol with cholesterol oxidase followed by the spectrometric detection using peroxidase of hydrogen peroxidase that is a product of the enzymatic reaction of cholesterol with cholesterol oxidase.

* * * * *

UNITED STATES PATENT AND TRADEMARK OFFICE
CERTIFICATE OF CORRECTION

PATENT NO.    : 6,986,998 B2
DATED         : January 17, 2006
INVENTOR(S)   : Kishi et al.

Page 1 of 1

It is certified that error appears in the above-identified patent and that said Letters Patent is hereby corrected as shown below:

Column 8,
Line 7, change "or the thereof" to -- or the salt thereof --.

Signed and Sealed this

Twenty-eighth Day of March, 2006

JON W. DUDAS
*Director of the United States Patent and Trademark Office*